United States Patent [19]

Yamaguchi et al.

[11] Patent Number: 5,270,188

[45] Date of Patent: Dec. 14, 1993

[54] **PREPARATION OF GLYCERIDES HAVING A HIGH CONTENT OF MONGLYCERIDES WITH A LIPASE FROM *PENICILLIUM CYCLOPIUM* ATCC 34613**

[75] Inventors: Shotaro Yamaguchi, Nishiharu; Tamio Mase, Ichinomiya; Satoru Asada, Iwakura, all of Japan

[73] Assignee: Amano Pharmaceutical Co., Ltd., Aichi, Japan

[21] Appl. No.: 793,283

[22] Filed: Nov. 12, 1991

Related U.S. Application Data

[63] Continuation of Ser. No. 360,530, Jun. 2, 1989, abandoned, which is a continuation of Ser. No. 763,661, Aug. 8, 1985, abandoned.

[30] Foreign Application Priority Data

Feb. 6, 1985 [JP] Japan .................. 60-21546

[51] Int. Cl.$^5$ ................ C12N 9/20; C12P 7/64
[52] U.S. Cl. ................... 435/134; 435/198; 435/262; 435/280; 435/933
[58] Field of Search .............. 435/134, 198, 262, 280, 435/933

[56] References Cited

FOREIGN PATENT DOCUMENTS 50-77586  6/1975  Japan .
1577933  10/1980  United Kingdom .

OTHER PUBLICATIONS

Tsujisaka et al., *Biochimica et Biophysica Acta*, 489, (1977), 415–422.
Okumura et al., *The Journal of Biochemistry*, vol. 87, No. 1, (1980), pp. 205–211.
Linfield et al., *Journal of the American Oil Chemists' Society*, vol. 61, No. 2, (Feb. 1984).
Okumura et al., *Agricultural and Biological Chemistry* vol. 45, (1981), pp. 185–189.
Lauridsen, "Food Emulsifiers: Surface Activity, Edibility, Manufacture, Composition, and Application" *J. Am. Oil Chemists' Soc.*, Jun. 1976 (vol. 53), pp. 400–407.

*Primary Examiner*—David M. Naff
*Assistant Examiner*—L. Blaine Lankford
*Attorney, Agent, or Firm*—Wegner, Cantor, Mueller & Player

[57] ABSTRACT

A glyceride produce free from triglycerides and containing mostly monoglycerides is made by mixing glycerol and fatty acids with a lipase which is isolated from *Penicillium cyclopium* ATCC 34613.

11 Claims, 1 Drawing Sheet

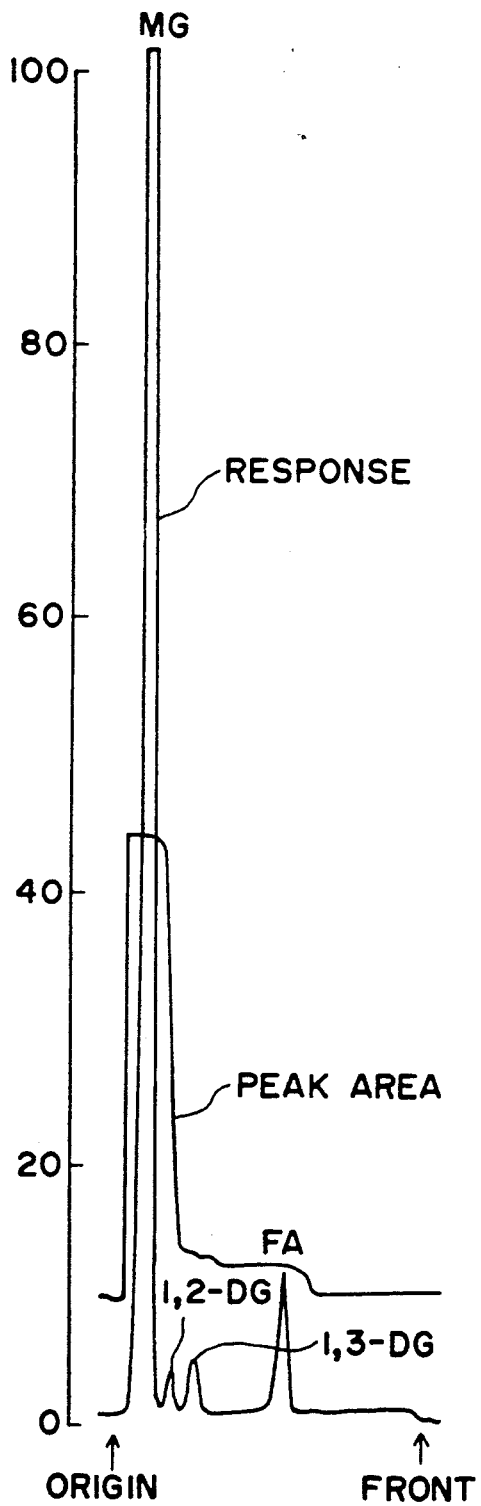

PREPARATION OF GLYCERIDES HAVING A HIGH CONTENT OF MONGLYCERIDES WITH A LIPASE FROM *PENICILLIUM CYCLOPIUM* ATCC 34613

This application is a continuation of U.S. application Ser. No. 07/360,530 filed Jun. 2, 1989 now abandoned, which is a continuation of U.S. application Ser. No. 763,661 filed Aug. 8, 1985, now abandoned.

BACKGROUND OF THE INVENTION

1. Field of the Invention

This invention relates to a process for producing glycerides using an enzyme. More particularly, the present invention relates to a process for synthesizing glycerides by reacting a fatty acid or a fatty acid ester with glycerol in the presence of a lipase, wherein, as the lipase, a monoglyceride lipase and/or a diglyceride lipase is used to produce glycerides containing little or no triglyceride and consisting substantially of a monoglyceride and a diglyceride. Most preferably, the present invention relates to a process for synthesizing glycerides by reacting a fatty acid or a fatty acid ester with glycerol in the presence of a lipase, wherein the above mentioned lipase is used to produce glycerides completely or substantially free from triglyceride and diglyceride and consisting substantially of a monoglyceride. Monoglycerides and diglycerides are useful as emulsifiers and antimicrobial agents.

2. Description of the Prior Art

Lipases are enzymes which hydrolyze fats and oils and esters of fatty acids. However, it is known that, under certain conditions, lipases cause an esterification reaction which is the reverse of hydrolysis and thereby glycerides or esters can be synthesized from a fatty acid and glycerol or from a fatty acid and an alcohol (J. Gen. Appl. Microbiol., 10, 13–22, 1964; Proc. IV IFS: Ferment. Technol. Today, 315–320, 1972, issued by Society of Fermentation Technology Japan; Biochim. Biophys. Acta, 489, 415–422, 1977; Bull. Tech/Gattefosse Rep., 76, 34–36, 1983; J. Am. Oil Chem. Soc., 61, 191–195, 1984; Japanese Patent Publication No. 7754/1976, Japanese Patent Publication No. 23535/1982, Japanese Patent Laid-Open No. 118094/1984, Japanese Patnet Laid-Open No. 118095/1984, etc.). The lipases used in this prior art and the most popular lipases are so-called triacylglycerol lipases which are also called triglyceride lipases. These lipases have a specificity not only to triglycerides but also to diglycerides and monoglycerides, although the specificities each glyceride are different. Glycerides synthesized by the esterification reaction using the action of these triglyceride lipases are usually a mixture of a triglyceride, a diglyceride, and a monoglyceride and, even when these glycerides consist substantially of a monoglyceride and a diglyceride, the content of monoglyceride in the glyceride mixture is low.

Monoglycerides and diglycerides are in wide use as emulsifiers for foods, cosmetics, medicines, etc. It is known that, in the ability to act as an emulsifier, monoglycerides are far superior to diglycerides and the presence of triglycerides is not desirable. Particular types of monoglycerides such as monolaurin, monocaprin and the like are in use as antimicrobial agents or an antiseptic agents, e.g. for foods. In general, glycerides used as emulsifiers are required to contain at least about 90 mole % of monoglycerides. Hence, in the conventional production of such glycerides, it has been necessary to subject a glyceride mixture to molecular distillation or the like to enhance the content of monoglycerides.

SUMMARY OF THE INVENTION

The object of the present invention is to provide a process for producing glycerides consisting substantially of a monoglyceride and a diglyceride, useful as emulsifiers and antimicrobial agents, as well as to provide a process for producing glycerides consisting substantially of a monoglyceride.

According to the present invention, a fatty acid or a fatty acid ester is reacted with glycerol in the presence of a monoglyceride lipase and/or a diglyceride lipase, whereby are produced glycerides containing little or no triglyceride and consisting substantially of a monoglyceride and a diglyceride.

Further, according to the present invention, a fatty acid or a fatty acid ester is reacted with glycerol in the presence of a monoglyceride lipase and/or a diglyceride lipase, under such preferred conditions that the formation of diglyceride and triglyceride is minimized, so as to produce a glyceride completely or substantially free from triglycerides and diglycerides and consisting substantially of monoglyceride.

According to one aspect of the present invention, there is provided a process for producing monoglycerides and diglycerides substantially free from triglycerides which comprises mixing glycerol with a fatty acid or an ester of fatty acid and agitating the mixture in presence of a monoglyceride lipase and/or a diglyceride lipase.

According to another aspect of the present invention, there is provided a process for producing monoglycerides substantially free from triglycerides and diglycerides which comprises mixing glycerol with a fatty acid or an ester of fatty acid and agitating the mixture in presence of a monoglyceride lipase and/or a diglyceride lipase.

BRIEF DESCRIPTION OF THE DRAWING

The accompanying drawing illustrates the glycerides composition prepared according to the present process, analyzed using thin-layer chromatography using a hydrogen flame ionization detector.

In the drawing, MG is a monoglyceride; 1,2-DG is a 1,2-diglyceride; 1,3-DG is a 1,3-diglyceride; and FA is a fatty acid.

DETAILED DESCRIPTION OF PREFERRED EMBODIMENTS OF THE INVENTION

According to the present invention, a fatty acid or a fatty acid ester is reacted with glycerol in the presence of a monoglyceride lipase and/or a diglyceride lipase under appropriate conditions, whereby glycerides are synthesized completely or substantially free from triglyceride or triglyceride and diglyceride.

The lipase used in the present invention is an enzyme which can hydrolyze a monoglyceride wherein either one of the three hydroxyl groups of glycerol is esterified with a fatty acid and/or a diglyceride wherein the two hydroxyl groups at the 1,2- or 1,3- or 2,3-positions of glycerol are esterified with a fatty acid but has little or no effect on triglycerides wherein all three hydroxyl groups of glycerol are esterified by fatty acid. As examples of such a lipase, there are mentioned monoglyceride lipases and diglyceride lipases both obtained from internal animal organs, such as rat small intestine, porcine adipose tissue and the like, as well as lipases having a specificity to monoglycerides and diglycerides produced by moulds of the genus Penicillium. Preferred in the present invention are lipases from genus Penicillium and particularly preferred is a lipase produced by *Penicillium cyclopium* deposited at the American Type Culture Collection under the accession number of ATCC 34613. This strain is listed in the ATCC catalogue and is available to any person.

It is known that, besides producing a triglyceride lipase, *Penicillium cyclopium* produces a lipase having a specificity for monoglycerides and diglycerides (J. Biochem., 87, 205-211, 1980). However, the present inventors do not know any literature suggesting that said lipase is usable for the object of the present invention.

In preparing a lipase used in the present invention, a strain of genus Penicillium capable of producing a lipase having a specificity for monoglycerides and/or diglycerides is grown in a medium used in ordinary cultivation of microorganisms and the lipase accumulated in the cultivation mixture is collected. Purification of the lipase collected from the cultivation mixture can be conducted using known purification means; however, for the object of the present invention, there is no need of purifying said lipase to a pure state. Only in case a crude lipase contains a triglyceride lipase, the triglyceride lipase must be removed. Although a cultivation mixture obtained with *Penicillium cyclopium* ATCC 34613 preferably used in the present invention contains a triglyceride lipase, this lipase can be separated and removed by subjecting a crude enzyme solution prepared from the cultivation mixture to chromatography, particularly preferably chromatography using DEAE-Sepharose CL-6B.

In the present invention, as the fatty acid and the ester thereof used as a raw material for glycerides synthesis, there are useful saturated or unsaturated fatty acids of 4 to 22 carbon atoms, methyl, ethyl, propyl, butyl, benzyl, amyl, vinyl and other esters of said fatty acids and their mixtures. There also useful are hydrolyzates of fats and oils obtained by physicochemical means such as an autoclave process, the Twitchell method, saponification and the like or by an enzymatic means using a triglyceride lipase. These fatty acids and esters thereof can have a straight or branched chain. Preferable fatty acids are, for example, stearic acid, oleic acid, linoleic acid, linolenic acid, palmitic acid, myristic acid, lauric acid, capric acid, caprylic acid, caproic acid, and isostearic acid. Preferable esters of fatty acid are, for example, vinyl stearate, vinyl palmitate, vinyl laurate, and vinyl caprate.

According to the present invention, one of the above fatty acids or one of the above esters thereof or their mixture is reacted with glycerol in the presence of a monoglyceride lipase and/or a diglyceride lipase under agitation at a temperature of 20° to 55° C., for 1 hour to 5 days, and at a water content in the reaction mixture of about 30% by weight or less, whereby glycerides are synthesized containing little or no triglyceride and consisting substantially of a monoglyceride and a diglyceride. The amount of lipase used is preferably 2 to 10,000 units per mole of fatty acid or ester thereof used as raw material. The ratio of glycerol to fatty acid or ester thereof is preferably 0.2 to 200 in terms of molar ratio. The pH employed during the reaction can be within a range where the lipase used acts effectively. It was ascertained that, when a most preferable lipase of *Penicillium cyclopium* ATCC 34613 is used, no triglyceride is synthesized.

According to the present invention, the ratio of monoglyceride and diglyceride in glycerides synthesized can be varied widely by selecting reaction conditions appropriately. Thus, the ratio of monoglyceride in glycerides can vary from about 50% (molar ratio) to substantially 100%. In order to synthesize substantially only a monoglyceride, it is preferable that the reaction time be 1 to 50 hours, the amount of lipase used be 2 to 5,000 units per mole of fatty acid or ester thereof used as raw material and the ratio of glycerol to fatty acid or ester thereof used as raw material be 0.2 to 50 in terms of molar ratio. In this case, requirements for water content in reaction mixture, reaction temperature, and pH are as mentioned previously.

The glyceride mixture synthesized according to the present process can be separated from a reaction mixture by extracting it with an organic solvent such as petroleum ether or the like, followed by vacuum distillation or alkaline refining to remove fatty acids. The unreacted raw material can be used again as a raw material for glycerides synthesis. When the glycerides obtianed contain a sufficiently high proportion of a monoglyceride, the mixture per se can be utilized as an emulsifier or an anti-microbial agent. Of the monoglyceride content is not sufficient, the glycerides can be utilized for the purpose after being subjected to a means such as the molecular distillation or the like to enhance the monoglyceride content. As mentioned already, according to the present inveniton, it is possible to synthesize glycerides consisting substantially of monoglyceride only; therefore, in this case, a treatment by molecular distillation or the like is unnecessary.

In the accompanying drawing, there is shown a typical example of composition analysis for glycerides synthesized from oleic acid and glycerol according to the present invention. After completion of the reaction between oleic acid and glycerol, the reaction mixture was subjected to extraction with petroleum ether and then the components in the resulting extract were analyzed employing thin-layer chromatography on silica gel using a hydrogen flame ionization detector (Iatroscan TH-10 manufactured by Iatron Laboratories, Inc.). As is clear from the drawing, the components in the glyceride obtained are mostly a monoglyceride (MG, namely, monoolein); a 1,2-diglyceride (1,2-DG, namely, 1,2-diolein) and a 1,3-diglyceride (1,3-DG, namely, 1,3-diolein) are present in small amounts and no triglyceride (namely, triolein) was synthesized. In the drawing, FA implies unreacted oleic acid.

The present invention will be explained in detail below by referring to Experiments and Examples. Analysis of glycerides synthesized as well as measurement of the proportion of a fatty acid or an ester thereof consumed in glyceride synthesis (hereinunder this proportion is referred to as consumption rate) were made as follows. Also, the definition of unit of lipase is given below.

Composition Analysis of Gylcerides Synthesized

The reaction mixture was extracted with petroleum ether. The components in the resulting extract were subjected to a preparative silica gel thin-layer plate (PLK 5 manufactured by Whatman Co.). Development was conducted with petroleum ether: diethyl ether: acetic acid (80:30:1 by volume) and spots were detected with iodine vapor. Each spot containing one glyceride was recovered and subjected to quantitative determination of each particular glyceride using a reagent composition (Triglyceride G-test Wako, manufactured by Wako Pure Chem. Ind., Ltd.) for enzymatic triglyceride determination using a triglyceride lipase, glycerol kinase, glycerol-3-phosphate oxidase and peroxidase. The proportion of each molecule species was expressed as mole %.

Consumption Rate of Raw Material Fatty Acid or Ester thereof

The reaction mixture was extracted with petroleum ether and the components in the resulting extract were analyzed with the above mentioned thin-layer chromatography using hydrogen flame ionization detector. The consumption rate of raw material fatty acid or ester thereof was expressed as percentile proportion of the sum of the peak area of glycerides obtained to the total peak area of glycerides obtained and unreacted fatty acid or ester thereof.

Definition of Unit of Lipase 0.95 ml of 50 mM acetate buffer solution (pH 5.6) containing 2.5 mM p-nitrophenyllaurate and 2.0% Triton X-100 was mixed with 0.05 ml of an enzyme solution. Incubation was conducted for 15 min at 37° C. and then 2.0 ml of acetone was added to quench the reaction. Thereafter, the amount of p-nitrophenol liberated in the reaction was determined from an absorbance at 410 nm. The amount of lipase required for liberating $1\mu$ mole p-nitrophenol per min in the above reaction was defined as 1 unit.

EXPERIMENT 1

Preparation of Lipase Having a Specificity for Monoglycerides and Diglycerides

*Penicillium cyclopium* ATCC 34613 was inoculated into a liquid medium (pH 6.0) containing 2% of rice bran and 1.5% of corn steep liquor and cultivation was conducted for 2 days at 26° C. with stirring and aeration. From the resulting cultivation mixture mycelia was removed by filtration. The resulting filtrate was subjected to ultrafiltration for concentration. The resulting concentrate was subjected to chromatography using DEAE-Sepharose CL-6B manufactured by Pharmacia Co. to separate and remove a triglyceride lipase present and to obtain a purified lipase preparation. It was ascertained that this lipase preparation hydrolyzes monoglycerides and diglycerides but has little hydrolyzing activity on triglycerides.

In the following, this lipase preparation was used.

EXPERIMENT 2

Relation between Reaction Time and Composition of Glycerides Synthesized 1.77 g of oleic acid, 8.0 g of glycerol, 0.2 ml (5 units) of a solution containing a lipase from *Penicillium cyclopium* and 0.35 ml of water were mixed. The reaction was conducted at 40° C. with stirring. At 8, 24, 48 and 96 hrs. after the start of the reaction, samples of reaction mixtures at these points of time were collected to conduct composition analysis of respective glycerides formed. As shown in Table 1, each glyceride mixture obtained consisted of only a monoglyceride and a diglyceride and no triglyceride was detected. The proportion of monoglyceride reached 70% or more, and the shorter the reaction time, the higher was the monoglyceride content.

TABLE 1

| Reaction time (hr) | Monoglyceride (%) | Diglyceride (%) | Triglyceride (%) |
|---|---|---|---|
| 8 | 95.6 | 4.4 | 0 |
| 24 | 90.7 | 9.3 | 0 |
| 48 | 78.9 | 21.1 | 0 |
| 72 | 78.4 | 21.6 | 0 |
| 96 | 73.3 | 26.8 | 0 |

EXPERIMENT 3

Relation between Amount of Lipase Used and Composition of Glycerides Synthesized In Experiment 2, the amount of lipase used was varied widely and the reaction was conducted for 20 hours at 40° C. As shown in Table 2, the smaller the amount of lipase used, the higher was the content of monoglyceride synthesized.

TABLE 2

| Amount of lipase used (unit) | Monoglyceride (%) | Diglyceride (%) | Triglyceride (%) |
|---|---|---|---|
| 1.25 | 97.5 | 2.5 | 0 |
| 5.0 | 93.7 | 6.4 | 0 |
| 15.0 | 78.0 | 22.0 | 0 |
| 30.0 | 65.6 | 34.4 | 0 |
| 50.0 | 54.4 | 45.6 | 0 |

EXPERIMENT 4

Relation between (a) Ratio of Raw Materials (Fatty Acid versus Glycerol) and (b) Compositon of Glycerides Synthesized In Experiment 2, the proportion of oleic acid and glycerol was varied widely and the reaction was conducted for 20 hours at 40° C. As shown in Table 3, the smaller the proportion of glycerol to fatty acid, the higher was the content of monoglyceride synthesized.

TABLE 3

| Oleic acid: Glycerol (g):(g) (Molar ratio) | Monoglyceride (%) | Diglyceride (%) | Triglyceride (%) |
|---|---|---|---|
| 0.95:9.0 (1:29.0) | 70.1 | 29.9 | 0 |
| 1.9:8.0 (1:12.9) | 86.5 | 13.5 | 0 |
| 3.8:6.0 (1:4.8) | 89.4 | 10.6 | 0 |
| 5.6:4.0 (1:2.2) | 95.1 | 4.9 | 0 |

EXAMPLE 1

1.77 g of oleic acid, 8.0 g of glycerol, and 0.2 ml (5 units) of a solution containing a lipase from *Penicillium cyclopium* were mixed, and the reaction was conducted for 20 hours at 30° C. The consumption rate of oleic acid was 47%. The resulting glycerides were extracted with petroleum ether analyzed for composition. The proportion of monoglyceride in total glycerides was 98.4% and that of diglyceride was 1.6%. No triglyceride was detected.

EXAMPLE 2

0.44 g of oleic acid, 9.5 g of glycerol, and 0.2 ml (5 units) of a solution containing a lipase from *Penicillium cyclopium* were mixed and the reaction was conducted for 20 hours at 40° C. The consumption rate of oleic acid was 75% and the glycerides synthesized consisted of 88.2% of monoglyceride, 11.8% of diglyceride and 0% of triglyceride.

EXAMPLE 3

1.77 g of oleic acid, 8.0 g of glycerol, 0.05 ml (5.5 units) of a solution containing a lipase from *Penicillium cyclopium* and 0.05 ml of water were mixed, and the reaction was conducted for 20 hours at 30° C. The consumption rate of oleic acid was 23% and the glycerides synthesized consisted of 94.9% of monoglyceride, 5.1% of diglyceride and 0% of triglyceirde.

EXAMPLE 4

1.77 g of lauric acid or capric acid, 8.0 g of glycerol, 0.2 ml (5 units) of a solution containing a lipase from *Penicillium cyclopium*, and 0.35 ml of water were mixed, and the reaction was conducted for 20 hours at 40° C. The consumption rate of fatty acid and the compositon of glycerides synthesized are shown in Table 4.

TABLE 4

| Raw material fatty acid | Consumption rate of fatty acid (%) | Mono- glyceride (%) | Di- glyceride (%) | Tri- glyceride (%) |
| --- | --- | --- | --- | --- |
| Lauric acid | 30 | 95.8 | 4.2 | 0 |
| Capric acid | 41 | 95.2 | 4.8 | 0 |

EXAMPLE 5

1.76 g of linoleic acid or 1.75 g of linolenic acid or 1.78 g of isostearic acid, 8.0 g of glycerol, 0.2 ml (5 units) of a solution containing a lipase from *Penicillium cyclopium*, and 0.35 ml of 1M McIlvaine buffer solution (pH 6.0) were mixed, and the reaction was conducted for 20 hours at 40° C. The consumption rate of fatty acid and the composition of glycerides synthesized are shown in Table 5.

TABLE 5

| Raw material fatty acid | Consumption rate of fatty acid (%) | Mono- glyceride (%) | Di- glyceride (%) | Tri- glyceride (%) |
| --- | --- | --- | --- | --- |
| Linoleic acid | 59 | 91.1 | 8.9 | 0 |
| Linolenic acid | 47 | 91.9 | 8.1 | 0 |
| Isostearic acid | 22 | 95.8 | 4.2 | 0 |

EXAMPLE 6

1.77 g of stearic acid, palmitic acid, myristic acid, caprylic acid or caproic acid, 8.0 g of glycerol, 0.2 ml (5 units) of a solution containing a lipase from *Penicillium cyclopium*, and 0.35 ml of water were mixed, and the reaction was conducted for each mixture for 20 hours at 40° C. Each glyceride mixture synthesized consisted mostly of a monoglyceride. In each glyceride mixture, a diglyceride was present only in a trace amount and no triglyceride was detected.

EXAMPLE 7

1.0 g of oleic acid, 1.0 g of palmitic acid, 8.0 g of glycerol, 0.2 ml (5 units) of a solution containing a lipase from *Penicillium cyclopium*, and 0.35 ml of water were mixed, and the reaction was conducted for 20 hours at 40° C. The consumption rate of fatty acids was 28% and the glycerides synthesized consisted of 94.4% of monoglycerides, 5.6% of diglycerides, and 0% of triglycerides.

EXAMPLE 8

1.77 g of vinyl laurate, 8.0 g of glycerol, and 0.55 ml (41.3 units) of a solution containing a lipase from *Penicillium cyclopium* were mixed and the reaction was conducted for 20 hours at 40° C. The consumption rate of vinyl laurate was 94% and the glycerides synthesized consisted of 96.2% of monoglyceride, 3.8% of diglyceride and 0% of triglyceride.

EXAMPLE 9

1.77 g of vinyl caprate, 8.0 g of glycerol, 0.2 ml (5 units) of a solution containing a lipase from *Penicillium cyclopium*, and 0.35 ml of water were mixed, and the reaction was conducted for 20 hours at 40° C. The consumption rate of vinyl caprate was 91% and the glycerides synthesized consisted of 95.9% of monoglyceride, 4.1% of diglyceride and 0% of triglyceride.

EXAMPLE 10

1.77 g of vinyl palmitate or 1.95 g of vinyl stearate, 8.0 g of glycerol, 0.2 ml (13.8 units) of a solution containing a lipase from *Penicillium cyclopium*, and 0.35 ml of water were mixed and the reaction was conducted for each mixture for 5 hours at 40° C. For each reaction, the consumption rate of fatty acid ester and the composition of glycerides synthesized are shown in Table 6.

TABLE 6

| Raw material fatty acid ester | Consumption rate of fatty acid ester (%) | Mono- glyceride (%) | Di- glyceride (%) | Tri- glyceride (%) |
| --- | --- | --- | --- | --- |
| Vinyl palmitate | 75 | 94.2 | 5.8 | 0 |
| Vinyl stearate | 47 | 94.6 | 5.4 | 0 |

What is claimed is:

1. A process for producing glycerides essentially free from triglycerides and containing at least about 90% monoglycerides based on total glycerides, comprising mixing glycerol with a fatty acid or an ester of the fatty acid and agitating the mixture in the presence of a monoglyceride lipase from *Penicillium cyclopium* 34613 to produce glycerides essentially free from triglycerides and containing at least about 90% monoglycerides based on total glycerides, wherein the molar ratio of glycerol to fatty acids or ester of the fatty acid ranges from about 2.2 to 14.

2. A process according to claim 1, wherein the reaction is carried out for 1 to 50 hours with agitation.

3. A process according to claim 1, wherein lipase is used in an amount of 2 to 5,000 units per mole of raw material fatty acid or ester thereof.

4. A process according to claim 1, wherein the reaction temperature is 20° to 55° C.

5. A process according to cliam 1, wherien the water content in the reaction mixture is 30% by weight or less.

6. A process according to claim 1, wherein the fatty acid is a saturated or unsaturated fatty acid of 4 to 22 carbon atoms.

7. A process according to cliam 6, wherein the fatty acid has a straight chain.

8. A process according to cliam 6, wherein the fatty acid has a branched chain.

9. A process according to cliam 1, wherein the ester of fatty acid is selected from the group consisting of methyl, ethyl, propyl, butyl, benzyl, amyl, and vinyl esters of saturated or unsaturated fatty acids of 4 to 22 carbon atoms.

10. A process according to claim 9, wherein the ester of fatty acid has a straight chain in the fatty acid moiety.

11. A process according to claim 9, wherein the ester of fatty acid has a branched chain in the fatty acid moiety.

* * * * *